US008163788B2

(12) United States Patent
Famulok et al.

(10) Patent No.: US 8,163,788 B2
(45) Date of Patent: Apr. 24, 2012

(54) LOW-MOLECULAR INHIBITORS OF CYTOHESIN-FAMILY GUANINE NUCLEOTIDE EXCHANGE FACTORS

(75) Inventors: Michael Famulok, Bonn (DE); Waldemar Kolanus, Bonn (DE); Markus Hafner, Bonn (DE); Imke Grune, Koblenz (DE); Barbara Tappertzhofen, Cologne (DE); Mirko Theis, Bonn (DE)

(73) Assignee: Rheinische Friedrich-Wilhelms Universitat Bonn, Bonn (DE)

( * ) Notice: Subject to any disclaimer, the term of this patent is extended or adjusted under 35 U.S.C. 154(b) by 1090 days.

(21) Appl. No.: 11/667,046

(22) PCT Filed: Nov. 18, 2005

(86) PCT No.: PCT/EP2005/056084
§ 371 (c)(1),
(2), (4) Date: Oct. 12, 2007

(87) PCT Pub. No.: WO2006/053903
PCT Pub. Date: May 26, 2006

(65) Prior Publication Data
US 2009/0105286 A1    Apr. 23, 2009

(30) Foreign Application Priority Data

Nov. 19, 2004  (DE) .................. 10 2004 055 998

(51) Int. Cl.
*A61K 31/4196* (2006.01)
(52) U.S. Cl. ........................................... 514/384
(58) Field of Classification Search .................. 514/384
See application file for complete search history.

(56) References Cited

U.S. PATENT DOCUMENTS

| 6,221,841 B1 | 4/2001 | Czech et al. ........... 514/12 |
| 2004/0116490 A1 | 6/2004 | Marino, Jr. et al. ......... 514/383 |

FOREIGN PATENT DOCUMENTS

| WO | WO 02053731 | 7/2002 |
| WO | WO 02057240 | 7/2002 |
| WO | WO 2004030629 | 4/2004 |
| WO | WO2004/052280 A2 * | 6/2004 |

OTHER PUBLICATIONS

Julie G. Donaldson and Catherine L. Jackson, "Regulators and Effectors of the ARF GTPases", "Current Opinion in Cell Biology" vol. 12 : pp. 475-482 (2000).

Betz et al,. "Solution Structure of the Cytohesin-1 (B2-1) Sec7 Domain and its Interaction with the GTPase ADP Ribosylation Factor 1", Proc. Natl. Acad. Sci. USA vol. 95, pp. 7909-7914 (1998).
Chardin, et al., "A Human Exchange Factor for ARF Contains Sec 7- and Pleckstrin-Homology Domains", Nature, vol. 384 , pp. 481-484 (Dec. 1996).
Peyroche, et al., "Brefeldin A Acts to Stabilize an Abortive ARF-GDP-Sec7 Domain Protein Complex: Involvement of Specific Residues of the Sec7 Domain", Molecular Cell, vol. 3, pp. 275-285, (Mar. 1999).
Mayer, et al., "Controlling Small Guanine-Nucleotide-Exchange Factor Function Through Cytoplasmic RNA Intramers", Proc. Natl. Acad. Sci. USA, vol. 98, No. 9, pp. 4961-4965, (Apr. 24, 2001).
Theis, et al., "Discriminatory Aptamer Reveals Serum Response Element Transcription Regulated by Cytohesin-2", Proc. Natl. Acad. Sci. USA.. vol. 101, No. 31, pp. 11221-11226, (Aug. 3, 2004).
Kolanus, et al., "αLβ2 Integrin/LFA-1 Binding to ICAM-1 Induced by Cytohesin-1, a Cytoplasmic Regulatory Molecule", Cell, vol. 86, pp. 233-242, (Jul. 26, 1996).
Geiger, et al., "Cytohesin-1 Regulates β-2 Intergrin-Mediated Adhesion Through both ARF-GEF Function and Interaction with LFA-1," The EMBO Journal, vol. 19, No. 11, pp. 2525-2536, (2000).
Coligan, et al., Edts,"Purification and fragmentation of antibodies", Current Protocols in Immunology, Section III, Units 2.7.1-2.7.12 (1997).
Coligan, et al., "Preparation of human mononuclear cell populations and subpopulations", Current Protocols in Immunology, Section I, Unit 7.1.1-7.1.7 (1996).
Römpp Lexikon Chemie, "Pyrimethamin", pp. 3642, 4514, and 4635, (1999).
Louis Renault, et al., "Structural snapshots of the mechanism and inhibition of a guanine nucleotide exchange factor", Nature, vol. 426, pp. 525-530, (Dec. 4, 2003).
Naoko Morinaga, et al., "Cloning and expression of a cDNA encoding a bovine brain brefeldin A-sensitive guanine nucleotide-exchange protein for ADP-ribosylation factor", Proc. Natl. Acad. Sci. USA, vol. 94, pp. 12926-12931, (Nov. 1997).
Makoto Sata, "Structural basis for the inhibitory effect of brefeldin A on guanine nucleotide-exchange proteins for ADP-ribosylation factor", Proc. Natl. Acad. Sci. USA, vol. 96, pp. 2752-2757, Mar. 1999.
Jackson, et al., "Turning on ARF: the Sec7 Family of guanine-nucleotide-exchange factors", Trends in Cell Biology, vol. 10, (Feb. 2000).
Beilsteins Handbuch der Organischen Chemie, "Amino Derivate der Carbonsäuren CnH2nO2", p. 2358, (1980).

* cited by examiner

*Primary Examiner* — Jeffrey S. Lundgren
*Assistant Examiner* — Nelson Blakely, III
(74) *Attorney, Agent, or Firm* — Davidson, Davidson & Kappel, LLC

(57) ABSTRACT

The invention relates to a pharmaceutical composition and the use thereof, wherein the pharmaceutical composition contains compounds selected from a group of general formulas (5), (6), (7) and (8) and/or enantiomers, diastereomers or the pharmaceutically acceptable salts thereof. The pharmaceutical composition is used for treating autoimmune and tumoral diseases and/or for immunosupresion.

9 Claims, 5 Drawing Sheets

Fig. 3

Figure 1:
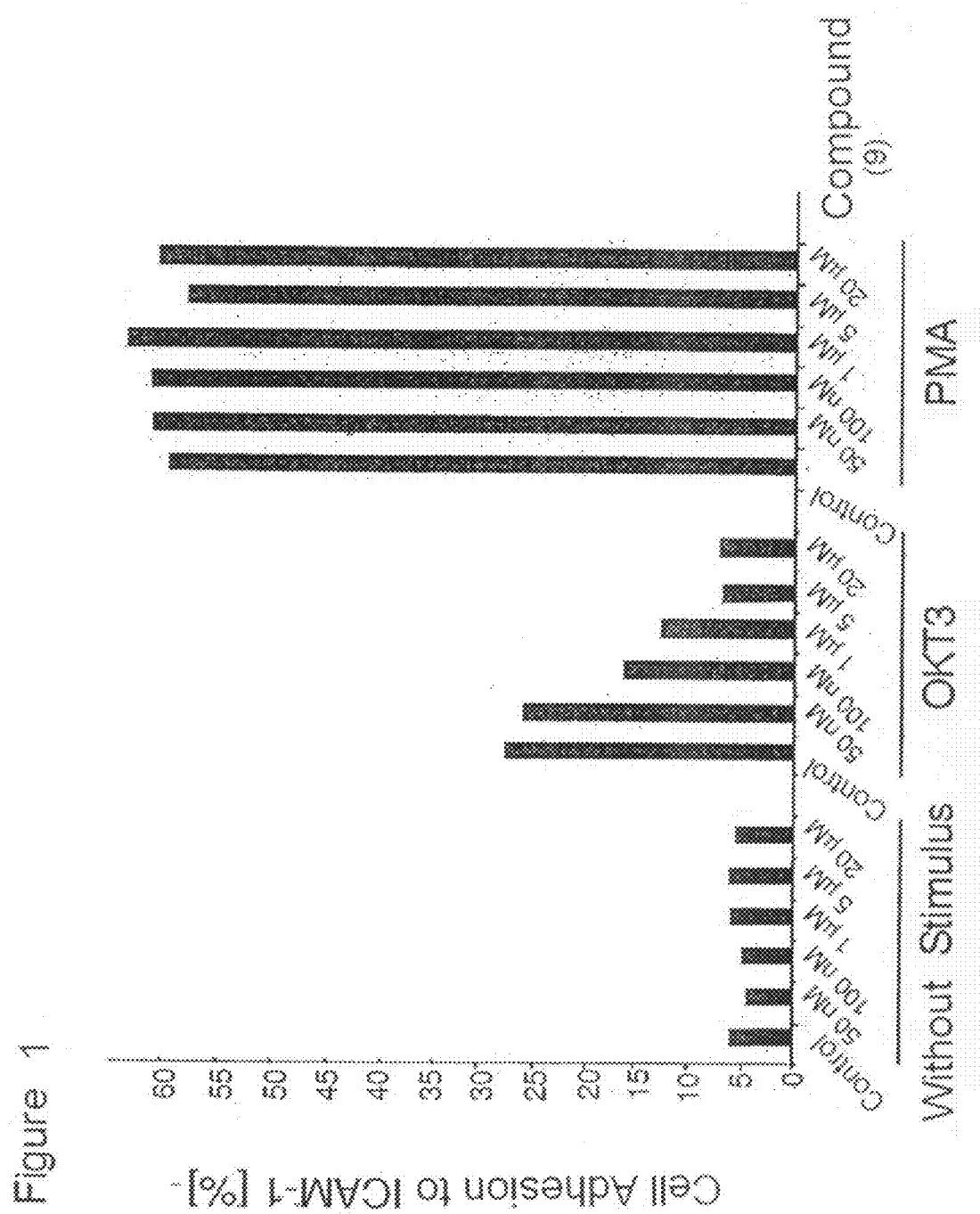

M69 Template Sequence: 5´-GGG AGA GAC AAG CTT GGG TCT ATT ATG CCT TTA GCT AGC GCA TTC TGT GGG GTG GGT GGA AGA AGA GAA AGA GAA GTT AAT TAA GGA TCC TCA G-3´ 93 nt 5´-Primer: 5´-<u>TCT AAT ACG ACT CAC TAT AGG</u> GAG AGA CAA GCT TGG GTC-3´

3´-Primer: 5´-CTG AGG ATC CTT AAT TAA CT-3´

LOW-MOLECULAR INHIBITORS OF CYTOHESIN-FAMILY GUANINE NUCLEOTIDE EXCHANGE FACTORS

The present invention relates to medical drugs. The drug can be used for the treatment of autoimmune diseases, tumor diseases and/or for immunosuppression.

Small G-proteins or GTPases and their regulatory proteins such as exchange factors regulate central cellular processes such as cell proliferation, cell adhesion and cell migration, programmed cell death or responses to cell stress. In spite of the sometimes very homologous structure of these regulatory proteins or exchange factors, they highly specifically fulfill different tasks in the context of the cell, whereby some proteins are selectively involved in the genesis of certain diseases.

Guanine nucleotide exchange factors, which will also be referred to below as GEFs, activate small G-proteins by stimulating the GDP/GTP exchange. Guanine nucleotide exchange factors are regulators of activation signals.

The guanine nucleotide exchange factors for small GTPases of the family of the ADP ribosylation factors (ARFs) include the family of the large guanine nucleotide exchange factors such as Gea1, Gea2, B1G1, B1G2, and the family of the small guanine nucleotide exchange factors, the cytohesins such as cytohesin-1, cytohesin-2, cytohesin-3 and cytohesin-4 (Julie G Donaldson and Catherine L Jackson, Regulators and effectors of the ARF GTPases, Current Opinion in Cell Biology 2000, 12:475-482).

A shared feature of the guanine nucleotide exchange factors for small GTPases of the family of the ADP ribosylation factors is their central sec7-domain, corresponding to the amino acids 62-244 in cytohesin-1 (Ref.: Betz et al, Proc Natl Acad Sci USA. 1998 Jul. 7; 95(14):7909-14), cytohesin-2 (Chardin, P. et al., Nature 384, 481-4 (1996) or Gea2 (Peyroche, A. et al., Mol Cell 3, 275-85 (1999)). The sec7-domain is largely similar within the guanine nucleotide exchange factors and is responsible for the catalysis of the guanine nucleotide exchange.

Cytohesins have a molecular weight of about 50 kDa and are involved in the regulation of cell proliferation/cell migration in cancer cells and immune cells.

Currently, the only known inhibitors for GEFs are Brefeldin A as well as RNA aptamers and peptides, and they are either highly toxic or insufficiently capable of entering cells, as a result of which they cannot be used medically. Consequently, exchange factors of the cytohesin family have not yet been usable as molecular target structures for medical applications. Other compounds that inhibit these proteins are not yet known in the state of the art.

The objective of the present invention was to provide compounds that can be used as inhibitors of the GEFs of the cytohesin family, drugs that comprise these compounds as well as their use for the treatment of diseases by means of these inhibitors.

This objective is achieved by a drug comprising compounds selected from the group comprising the general formulas (1), (2), (3), (4) and/or their enantiomers, diastereomers as well as their pharmaceutically well-tolerated salts:

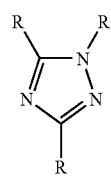

(1)

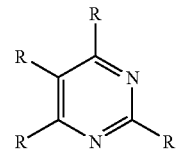

(2)

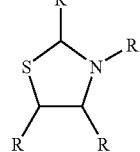

(3)

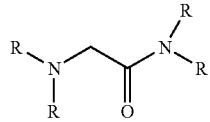

(4)

wherein:

R is selected from the group comprising hydrogen, OH, COOH, COO($C_1$-$C_{10}$-alkyl), $CONH_2$, CONH($C_1$-$C_{10}$-alkyl), CON($C_1$-$C_{10}$-alkyl)$_2$, halogen, preferably selected from the group comprising Cl, Br, F, amine, $C_1$-$C_{10}$-alkoxy and/or a structural element (A1), (B1), (C1), (D1), (E1), (F1), (G1), (H1), (I1), (J1) as shown below:

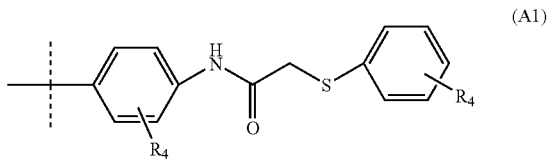

(A1)

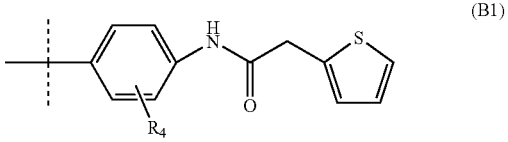

(B1)

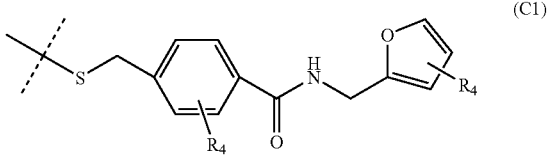

(C1)

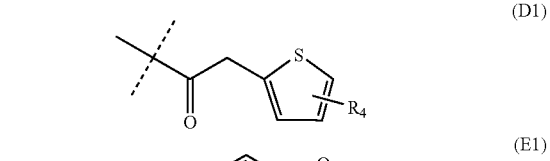

(D1)

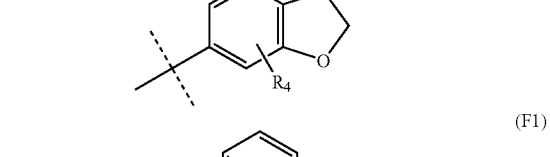

(E1)

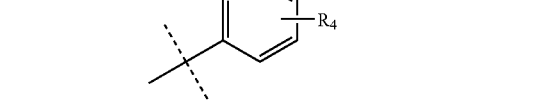

(F1)

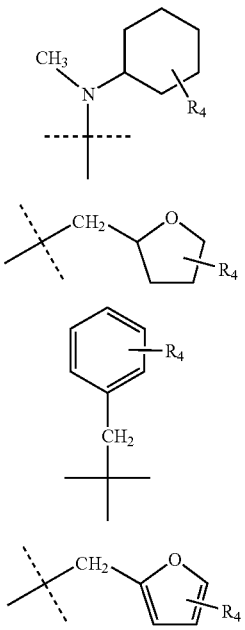

wherein:
R₄ is selected from the group comprising hydrogen, OH, COOH, COO($C_1$-$C_{10}$-alkyl), $CONH_2$, CONH($C_1$-$C_{10}$-alkyl), CON($C_1$-$C_{10}$-alkyl)₂, halogen, preferably selected from the group comprising Cl, Br, F, amine and/or $C_1$-$C_{10}$-alkoxy.

It was surprisingly found that compounds selected from the group comprising the general formulas (1), (2), (3), (4) can modulate the activity of the guanine nucleotide exchange factors, especially those of the family of the cytohesins, whereby the modulation is preferably a blocking or inhibition of the function. This is especially surprising since until now, no low-molecular inhibitors are known for this protein class.

A special advantage of the compounds selected from the group comprising the general formulas (1), (2), (3), (4) lies in the fact that they can inhibit the proteins at concentrations that are not toxic. Hence, the provided compounds, especially those selected from the group comprising the general formulas (1), (2), (3), (4), can be used in drugs and/or administered therapeutically.

Preferably, the compounds are low-molecular compounds. The term "low-molecular compounds" as set forth in this invention are compounds that preferably have a molecular weight in the range from 50 dalton to 800 dalton, preferably in the range from 100 dalton to 500 dalton, especially preferably in the range from 250 dalton to 475 dalton. Preferably, the compounds selected from the group comprising the general formulas (1), (2), (3), (4) have a molecular weight of less than 500 dalton.

Another major advantage of the drugs comprising the compounds selected from the group comprising the general formulas (1), (2), (3), (4) is achieved in that the compounds are capable of entering cells. The compounds are advantageously very capable of entering cells, as a result of which a very high availability of the compounds can be achieved at their site of action, especially in cells. The term "capable of entering cells" as set forth in this invention means that the compounds can pass through the cell membrane and can enter cells. In especially advantageous embodiments, the compounds enter the cells completely or almost completely and/or are completely or almost completely available in the cell.

This is especially advantageous since the drugs comprising compounds that are capable of entering cells and that are selected from the group comprising the general formulas (1), (2), (3), (4) can thus be administered with usual methods such as, for example, orally, dermally and/or intravenously, without the compounds having to be introduced into the cell by means of transfection.

In preferred embodiments, the drug comprises compounds selected from the group comprising the general formulas (1), (2), (3), (4), whereby the structural elements $R_1$, $R_2$ and/or $R_3$ are preferably selected from the sulfurous structural elements (A1), (B1), (C1) and/or (D1). In advantageous embodiments, the drug can contain compounds that have several of the same and/or different structural elements (A1), (B1), (C1) and/or (D1). Preferably, the compounds have one, preferably two, especially preferably three, of the same and/or different structural elements (A1), (B1), (C1) and/or (D1).

In preferred embodiments, the drugs contain compounds selected from the group comprising the general formulas (5), (6), (7), (8) as indicated below and/or their enantiomers, diastereomers as well as their pharmaceutically well-tolerated salts:

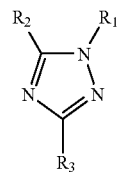 (5)

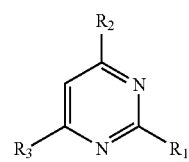 (6)

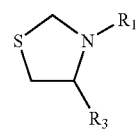 (7)

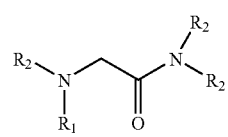 (8)

wherein:
$R_1$ is selected from the group comprising $R_2$, $R_3$ and/or a structural element (A2), (B2), (C2), (D2) as indicated below:

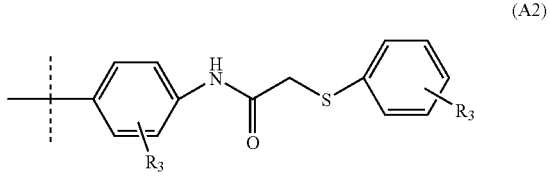 (A2)

(B2)
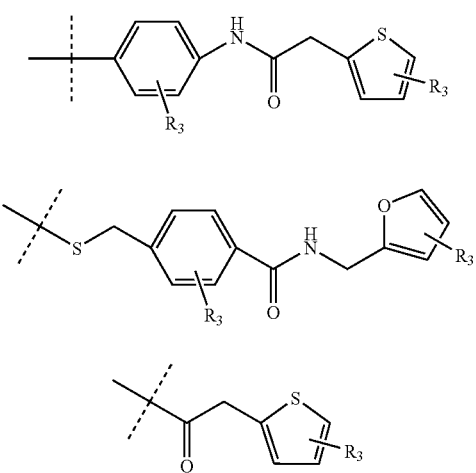
(C2)

(D2)

R₂ is selected from the group comprising R₁, R₃ and/or a structural element (E2), (F2), (G2), (H2), (I2), (J2), (K2) as indicated below:

(E2)
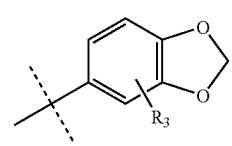

(F2)
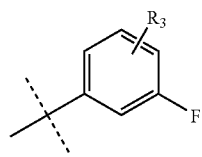

(G2)
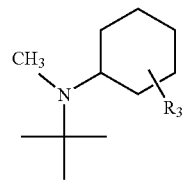

(H2)
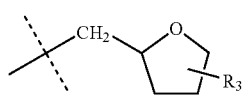

(I2)
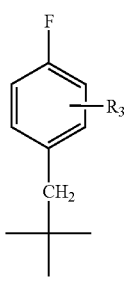

(J2)
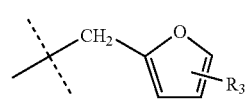

(K2)
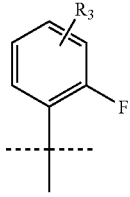

$R_3$ is selected from the group comprising $R_1$, $R_2$, and/or selected from the group comprising hydrogen, OH, COOH, COO($C_1$-$C_{10}$-alkyl), CONH$_2$, CONH($C_1$-$C_{10}$-alkyl), CON($C_1$-$C_{10}$-alkyl)$_2$, halogen, preferably selected from the group comprising Cl, Br, F, amine and/or $C_1$-$C_{10}$-alkoxy.

In other preferred embodiments, the drug comprises compounds selected from the group comprising the general formulas (5), (6), (7), (8), whereby the structural elements $R_1$, $R_2$ and/or $R_3$ are preferably selected from the sulfurous structural elements (A2), (B2), (C2) and/or (D2). In advantageous embodiments, the drug can contain compounds that have several of the same and/or different structural elements (A2), (B2), (C2) and/or (D2). Preferably, the compounds have at least one, preferably two, especially preferably three, of the same and/or different structural elements (A2), (B2), (C2) and/or (D2). Among the $C_1$-$C_{10}$-alkoxy groups, preference is given to methoxy groups and/or ethoxy groups.

Especially suitable drugs according to the invention comprise compounds selected from the group comprising the general formulas (5), (6), (7), (8) as indicated below and/or their enantiomers, diastereomers as well as their pharmaceutically well-tolerated salts:

(5)
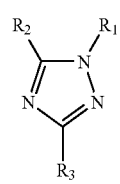

(6)
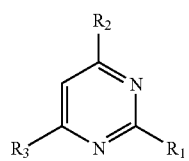

(7)
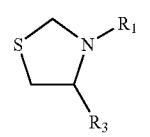

(8)
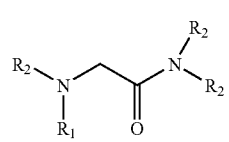

wherein:
$R_1$ is selected from the group comprising $R_2$, $R_3$ and/or a structural element (A3), (B3), (C3), (D3) as indicated below:

(A3)
(B3)
(C3)
(D3)

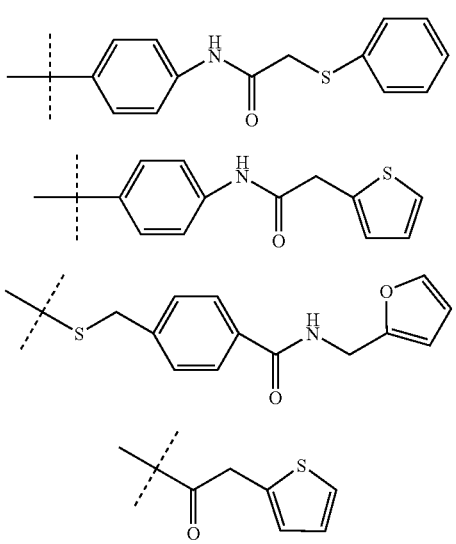

R₂ is selected from the group comprising $R_1$, $R_3$ and/or a structural element (E3), (F3), (G3), (H3), (I3), (J3), (K3), as indicated below:

(E3)
(F3)
(G3)
(H3)
(I3)
(J3)

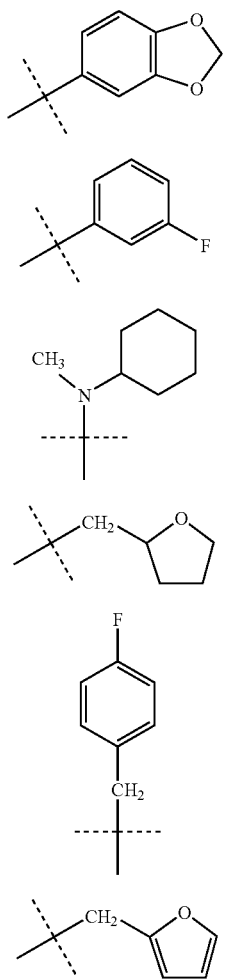

(K3)

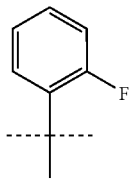

$R_3$ is selected from the group comprising $R_1$, $R_2$, and/or selected from the group comprising hydrogen, OH, COOH, COO($C_1$-$C_{10}$-alkyl), CONH₂, CONH($C_1$-$C_{10}$-alkyl), CON($C_1$-$C_{10}$-alkyl)₂, halogen, preferably selected from the group comprising Cl, Br, F, and/or $C_1$-$C_{10}$-alkoxy.

In especially preferred embodiments, the drug comprises compounds selected from the group comprising the general formulas (5), (6), (7), (8), whereby the structural elements $R_1$, $R_2$ and/or $R_3$ are preferably selected from the sulfurous structural elements (A3), (B3), (C3) and/or (D3). In advantageous embodiments, the drug can contain compounds that have several of the same and/or different structural elements (A3), (B3), (C3) and/or (D3). Preferably, the compounds have at least one, preferably two, especially preferably three, of the same and/or different structural elements (A3), (B3), (C3) and/or (D3).

In very especially preferred embodiments, the drug comprises compounds selected from the group comprising compounds (9), (10), (11), (12), (13), (14) as indicated below and/or their enantiomers, diastereomers as well as their pharmaceutically well-tolerated salts:

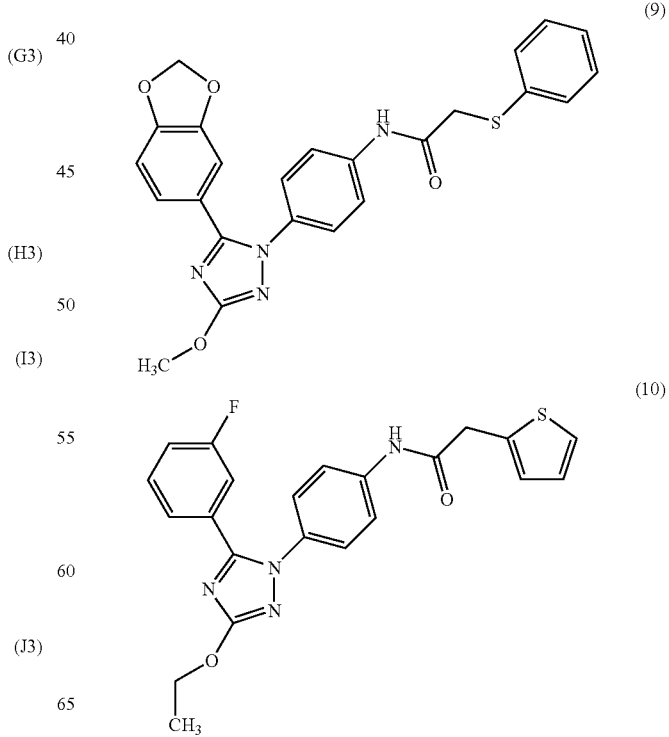

-continued

(11)
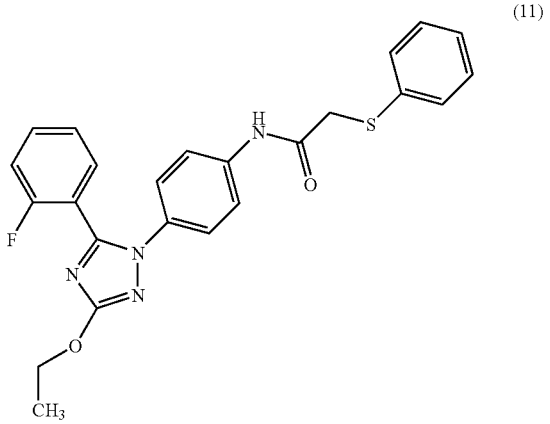

(12)
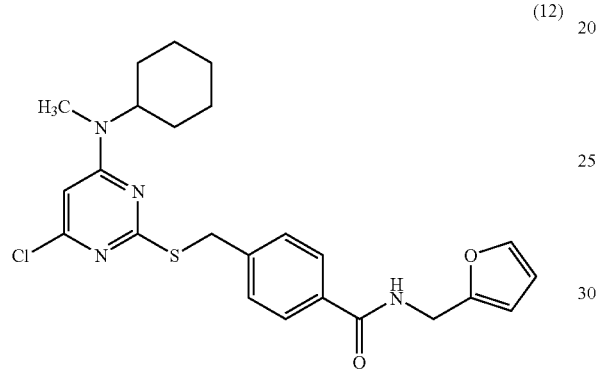

(13)
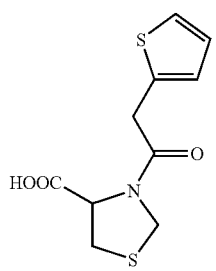

(14)
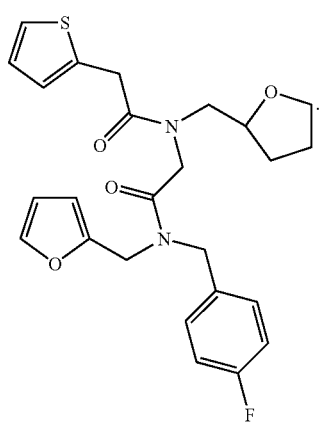

A preferred enantiomer of the compounds selected from the group comprising compounds (9), (10), (11), (12), (13) and/or (14) is the compound (19) as indicated below:

(19)
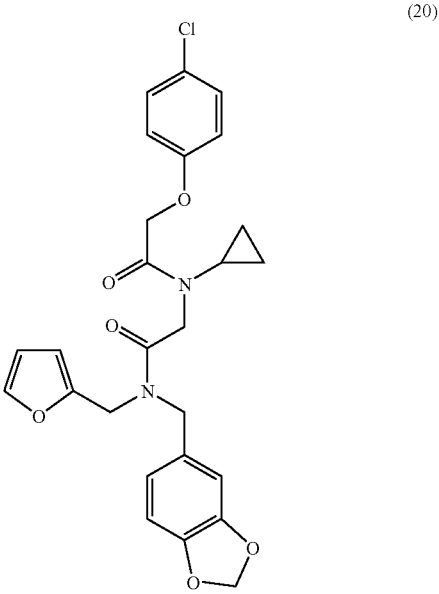

In other embodiments, the drug comprises compounds selected from the group comprising the general formulas (20) and/or (21) and/or their enantiomers, diastereomers as well as their pharmaceutically well-tolerated salts:

(20)
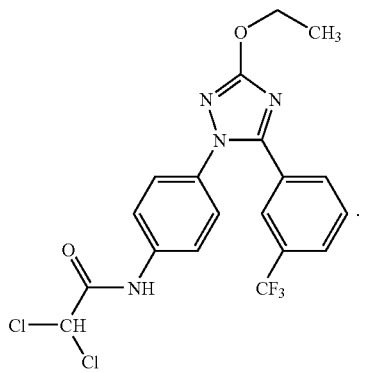

(21)

The drug can contain the compounds (20) and/or (21) as monomers and/or dimers, trimers and/or oligomers. The compounds selected from the group comprising the general formulas (20) and/or (21) preferably have dissociation constants in the range from 0.1 µM to 30 µM, especially preferably in the range from 0.5 µM to 10 µM, very especially preferably in the range from 1 µM to 7 µM. The compounds selected from the group comprising the general formulas (20) and/or (21) can have IC$_{50}$ values in the range from 0.1 µM to 30 µM, especially preferably in the range from 0.5 µM to 20 µM, very especially preferably in the range from 1 µM to 15 µM.

The drug according to the invention can have the compounds selected from the group comprising the general formulas (1), (2), (3), (4), (5), (6), (7) and/or (8) preferably selected from the group comprising compounds (9), (10), (11), (12), (13) and/or (14), (20) and/or (21) as monomers.

It can also be provided to at least partially join these compounds via suitable groups, which are also referred to as spacers, to several units comprising such monomers and to use dimers, trimers and/or oligomers of the compounds.

In other preferred embodiments, the drug has dimers, trimers and/or oligomers containing at least one or more of the monomers selected from the group comprising the general formulas (1), (2), (3), (4), (5), (6), (7) and/or (8), preferably selected from the group comprising compounds (9), (10), (11), (12) (13) and/or (14), (20) and/or (21).

The joining groups or spacers can join the individual units and/or monomers rigidly or flexibly. For example, the individual units and/or monomers can be joined rigidly by alkine groups, whereas a joining via one or more ethylene glycol group(s) can provide a flexible compound.

Preferably, monomers selected from the group comprising the general formulas (1), (2), (3), (4), (5), (6), (7) and/or (8) preferably selected from the group comprising compounds (9), (10), (11), (12), (13) and/or (14), (20) and/or (21) are at least partially joined with each other in order to form dimers, trimers and/or oligomers via ether, ester, alkine, amide, alkyl, alkenyl, cycloalkyl, alkoxy, alkylene, aryl, arylene and/or ethylene glycol groups.

Another advantage of the drug according to the invention can be achieved in that even small therapeutic dosages of the drug can be used. Since the compounds are highly capable at entering cells and are readily available, a high dosage, which can often lead to toxic side effects, can be avoided.

Preferably, the compounds selected from the group comprising the general formulas (1), (2), (3), (4), (5), (6), (7) and/or (8) preferably selected from the group comprising compounds (9), (10), (11), (12), (13) and/or (14), (20) and/or (21) have dissociation constants in the range from 0.1 µM to 30 µM, especially preferably in the range from 0.5 µM to 10 µM, very especially preferably in the range from 1 µM to 7 µM. Preferably, the dissociation constants are determined by means of micro-calorimetry. The dissociation constant preferably relates to the binding of the compounds to sec7-domains of the cytohesins.

In preferred embodiments, the compounds selected from the group comprising the general formulas (1), (2), (3), (4), (5), (6), (7) and/or (8) preferably selected from the group comprising compounds (9), (10), (11), (12), (13) and/or (14) have $IC_{50}$ values in the range from 0.1 µM to 30 µM, especially preferably in the range from 0.5 µM to 20 µM, very especially preferably in the range from 1 µM to 15 µM. The $IC_{50}$ value of the compounds for the inhibition of the exchange activity of the sec7-domains of various guanine nucleotide exchange factors corresponds to the concentration that is needed to reduce the activity of the protein to half.

A special advantage of the compounds provided and of the drugs containing these compounds can result from the fact that the compounds preferably leave the Golgi apparatus-dependent cellular functions intact. This especially entails an advantage over Brefeldin A, which destroys the Golgi apparatus of the cells.

In preferred embodiments, the drug, relative to a daily dosage, comprises 10 nM to 100 µM, preferably 100 nM to 10 µM, preferably 1 µM to 10 µM, especially preferably 1 µM to 3 µM of compound(s) selected from the group comprising the general formulas (1), (2), (3), (4), (5), (6), (7) and/or (8) preferably selected from the group comprising compounds (9), (10), (11), (12), (13) and/or (14) and/or their enantiomers, diastereomers as well as their pharmaceutically well-tolerated salts.

In other embodiments, the drug, relative to a daily dosage, comprises 10 nM to 100 µM, preferably 100 nM to 10 µM, preferably 1 µM to 10 µM, especially preferably 1 µM to 3 µM, also preferably 500 nM to 3 µM, also preferably 500 nM to 1 µM of compound(s) selected from the group comprising the general formulas (20) and/or (21) and/or their enantiomers, diastereomers as well as their pharmaceutically well-tolerated salts.

In other preferred embodiments, the drug, relative to a daily dosage, comprises 500 nM to 3 µM, preferably 500 nM to 1 µM of compound(s) selected from the group comprising the general formulas (1), (2), (3), (4), (5), (6), (7) and/or (8) preferably selected from the group comprising compounds (9), (10), (11), (12), (13) and/or (14), (20) and/or (21).

The term "daily dosage" as set forth in this application refers to the amount of the drug that is administered per day.

The compounds selected from the group comprising the general formulas (1), (2), (3), (4), (5), (6), (7) and/or (8) preferably selected from the group comprising compounds (9), (10), (11), (12), (13), (14) and/or (19), (20) and/or (21) can modulate the activity of guanine nucleotide exchange factors that have a sec7-domain, whereby the modulation is a blocking or inhibition.

Advantageously, compounds selected from the group comprising the general formulas (1), (2), (3), (4), (5), (6), (7) and/or (8) preferably selected from the group comprising compounds (9), (10), (11), (12), (13), (14) and/or (19), (20) and/or (21) and/or their enantiomers, diastereomers as well as their pharmaceutically well-tolerated salts can be used as inhibitors for proteins having at least one sec7-domain.

These compounds can be used as inhibitors for proteins having a sec7-domain, whereby the proteins are preferably selected from the group comprising guanine nucleotide exchange factors, preferably selected from the group comprising guanine nucleotide exchange factors for human ADP ribosylation factors, such as Gea1, Gea2, B1G1, B1G2 and/or cytohesins such as cytohesin-1, cytohesin-2, cytohesin-3 and/or cytohesin-4.

Surprisingly, it was found that the compounds selected from the group comprising the compounds (9), (10), (11), (12), (13), (14) and/or (19), (20) and/or (21) can be used especially for the inhibition of the cytohesins.

In preferred embodiments, an advantage of the compounds lies in the fact that these compounds can bind specifically to cytohesins. In particular at low concentrations of the compounds, preferably in the range from 10 nM to 10 µM, preferably in the range from 500 nM to 1 µM, the compounds can bind to cytohesins whereas, at these concentrations, the compounds hardly bind or do not bind at all to higher-molecular guanine nucleotide exchange factors such as Gea1, Gea2, B1G1, B1G2.

The binding constant for the binding of the compounds, especially of the compound (9), to the sec7-domains of human cytohesins, can lie in the range from 100 nM to 1500 nM, preferably in the range from 200 nM to 900 nM, preferably in the range from 200 nM to 500 nM.

In other preferred embodiments, the compounds can have a specificity for certain cytohesins, for example, compounds (12) can advantageously preferably bind to cytohesin-1 rather than to cytohesin-2.

Without being committed to a given theory, it is assumed that compounds according to the invention, which preferably bind cytohesin-1 rather than to cytohesin-3 and that consequently can specifically inhibit it, make it possible to use these compounds for treating Type 2 diabetes.

Particularly in insulin signaling, the inhibition constants ($K_i$ values) of the provided compounds can lie in the range from 7 μM to 20 μM with respect to cytohesins.

The specificity of the compounds can be influenced by the concentration of the compounds, for example, a specificity to certain cytohesins can occur at higher or lower concentrations of the compounds. This makes it possible to use the compounds in certain concentration ranges, in so-called therapeutic windows, for the inhibition of certain cytohesins.

Compounds selected from the group comprising the general formulas (15), (16), (17), (18) as indicated below and/or their enantiomers, diastereomers as well as their pharmaceutically well-tolerated salts:

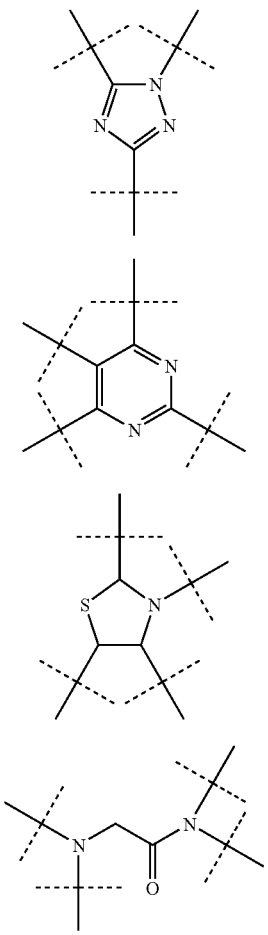

are advantageous for the production of inhibitors suitable for blocking proteins having at least one sec7-domain.

The term "blocking" as set forth in this invention means a binding of the compounds (15), (16), (17), (18) to the sec7-domain of the proteins which preferably leads to an inhibition of the proteins having a sec7-domain, especially of the cytohesins.

Here, the structural elements containing the compounds can be selected from the group comprising R, $R_1$, $R_2$, $R_3$, and/or $R_4$, structural elements (A1), (B1), (C1), (D1), (E1), (F1), (G1), (H1), (I1), (J1), (A2), (B2), (C2), (D2), (E2), (F2), (G2), (H2), (I2), (J2), (K2), (A3), (B3), (C3), (D3), (E3), (F3), (G3), (H3), (I3), (J3), (K3), hydrogen, OH, COOH, COO($C_1$-$C_{10}$-alkyl), $CONH_2$, CONH($C_1$-$C_{10}$-alkyl), CON($C_1$-$C_{10}$-alkyl)$_2$, halogen, preferably selected from the group comprising Cl, Br, F, amine, $C_1$-$C_{10}$-alkoxy, alkyl, alkenyl, alkinyl, alkoxy, aryl, alkylene, arylene, amines, halogen, carboxylate derivatives, cycloalkyl, carbonyl derivatives, heterocycloalkyl, heteroaryl, heteroarylene, sulphonate, sulphate, phosphonate, phosphate, phosphine and/or phosphine oxide, whereby, unless otherwise indicated:

alkyl is linear or branched $C_1$-$C_{20}$-alkyl, preferably ethyl, propyl, iso-propyl, tert-butyl, butyl, pentane,
alkenyl is $C_2$-$C_{20}$-alkenyl,
alkinyl is $C_2$-$C_{20}$-alkinyl,
cycloalkyl is $C_3$-$C_{10}$-cycloalkyl,
alkoxy is $C_1$-$C_6$-alkoxy,
alkylene is methylene; 1,1-ethylene; 1,2-ethylene; 1,1-propylidene; 1,2-propylene; 1,3-propylene; 2,2-propylidene; butan-2-ol-1,4-diyl; propan-2-ol-1,3-diyl; 1,4-butylene; cyclohexane-1,1-diyl; cyclohexane-1,2-diyl; cyclohexane-1,3-diyl; cyclohexane-1,4-diyl; cyclopentane-1,1-diyl; cyclopentane-1,2-diyl; and/or cyclopentane-1,3-diyl,
aryl is homo- or hetero-aromatic compounds with a molecular weight of =300,
arylene is 1,2-phenylene; 1,3-phenylene; 1,4-phenylene; 1,2-naphthalenylene; 1,3-naphthalenylene; 1,4-naphthalenylene; 2,3-naphthalenylene; 1-hydroxy-2,3-phenylene; 1-hydroxy-2,4-phenylene; 1-hydroxy-2,5-phenylene; and/or 1-hydroxy-2,6-phenylene,
heteroaryl is pyridinyl; pyrimidinyl; pyrazinyl; triazolyl; pyridazinyl; 1,3,5-triazinyl; quinolinyl; isoquinolinyl; quinoxalinyl; imidazolyl; pyrazolyl; benzimidazolyl; thiazolyl; oxazolidinyl; pyrrolyl; carbazolyl; indolyl; and/or isoindolyl,
heteroarylene is pyridindiyl; quinolindiyl; pyrazodiyl; pyrazolediyl; triazolediyl; pyrazinediyl; and/or imidazolediyl; especially pyridine-2,3-diyl; pyridine-2,4-diyl; pyridine-2,5-diyl; pyridine-2,6-diyl; pyridine-3,4-diyl; pyridine-3,5-diyl; quinoline-2,3-diyl; quinoline-2,4-diyl; quinoline-2,8-diyl; isoquinoline-1,3-diyl; isoquinoline-1,4-diyl; pyrazole-1,3-diyl; pyrazole-3,5-diyl; triazole-3,5-diyl; triazole-1,3-diyl; pyrazine-2,5-diyl; and/or imidazole-2,4-diyl,
$C_1$-$C_6$-heterocycloalkyl is piperidinyl; piperidine; 1,4-piperazine, tetrahydrothiophenes; tetrahydrofuran; 1,4,7-triazacyclononane; 1,4,8,11-tetraazacyclotetradecane; 1,4,7,10,13-pentaazacyclopentadecane; 1,4-diaza-7-thiacyclononane; 1,4-diaza-7-oxacyclononane; 1,4,7,10-tetraazacyclododecane; 1,4-dioxane; 1,4,7-trithiacyclononane; pyrrolidine; and/or tetrahydropyrane,
heterocycloalkylene is piperidin-1,2-ylene; piperidin-2,6-ylene; piperidin-4,4-ylidene; 1,4-piperazin-1,4-ylene; 1,4-piperazin-2,3-ylene; 1,4-piperazin-2,5-ylene; 1,4-piperazin-2,6-ylene; 1,4-piperazin-1,2-ylene; 1,4-piperazin-1,3-ylene; 1,4-piperazin-1,4-ylene; tetrahydrothiophen-2,5-ylene; tetrahydrothiophen-3,4-ylene; tetrahydrothiophen-2,3-ylene; tetrahydrofuran-2,5-ylene; tetrahydrofuran-3,4-ylene; tetrahydrofuran-2,3-ylene; pyrrolidin-2,5-ylene; pyrrolidin-3,4-ylene; pyrrolidin-2,3-ylene; pyrrolidin-1,2-ylene; pyrrolidin-1,3-ylene; pyrrolidin-2,2-ylidene; 1,4,7-triazacyclonon-1,4-ylene; 1,4,7-triazacyclonon-2,3-ylene; 1,4,7-triazacyclonon-2,9-ylene; 1,4,7-triazacyclonon-3,8-ylene; 1,4,7-triazacyclonon-2,2-ylidene; 1,4,8,11-tetraazacyclotetradec-1,4-ylene; 1,4,8,11-tetraazacyclotetradec-1,8-ylene; 1,4,8,11-tetraazacyclotetradec-2,3-ylene; 1,4,8,11-tetraazacyclotetradec-2,5-ylene; 1,4,8,11-tetraazacyclotetradec-1,2-ylene; 1,4,8,11-tetraazacyclotetradec-2,2-ylidene; 1,4,7,10-tetraazacyclododec-1,4-ylene; 1,4,7,10-tetraazacyclododec- 1,7-ylene; 1,4,7,10-tetraazacyclododec-1,2-ylene; 1,4,7,10-tetraazacyclododec-2,3-ylene; 1,4,7,10-tetraazacyclododec-2,2-ylidene; 1,4,7,10,13-pentaazacyclopentadec-1,4-ylene; 1,4,7,10,13-pentaazacyclopentadec-1,7-ylene; 1,4,7,10,13-pentaazacyclopentadec-2,3-ylene; 1,4,7,10,13-pentaazacyclopentadec-1,2-ylene; 1,4,7,10,13-pentaazacyclopentadec-2,2-ylidene; 1,4-diaza-7-thia-cyclonon-1,4-ylene; 1,4-diaza-7-thia-cyclonon-1,2-ylene; 1,4-diaza-7-thia-cyclonon-2,3-ylene; 1,4-diaza-7-thia-cyclonon-6,8-ylene; 1,4-diaza-7-thia-cyclonon-2,2-ylidene; 1,4-diaza-7-oxa-cyclonon-1,4-ylene; 1,4-diaza-7-oxa-cyclonon-1,2-ylene; 1,4-diaza-7-oxa-cyclonon-2,3-ylene; 1,4-diaza-7-oxa-cyclonon-6,8-ylene; 1,4-diaza-7-oxa-cyclonon-2,2-ylidene; 1,4-dioxan-2,3-ylene; 1,4-dioxan-2,6-ylene; 1,4-dioxan-2,2-ylidene; tetrahydropyran-2,3-ylene; tetrahydropyran-2,6-ylene; tetrahydropyran-2,5-ylene; tetrahydropyran-2,2-ylidene; 1,4,7-trithia-cyclonon-2,3-ylene; 1,4,7-trithia-cyclonon-2,9-ylene; and/or 1,4,7-trithia-cyclonon-2,2-ylidene, heterocycloalkyl is pyrrolinyl; pyrrolidinyl; morpholinyl; piperidinyl; piperazinyl; hexamethylene imine; 1,4-piperazinyl; tetrahydrothiophenyl; tetrahydrofuranyl; 1,4,7-triazacyclononanyl; 1,4,8,11-tetraazacyclotetradecanyl; 1,4,7,10,13-pentaazacyclopentadecanyl; 1,4-diaza-7-thiacyclononanyl; 1,4-diaza-7-oxa-cyclononanyl; 1,4,7,10-tetraazacyclododecanyl; 1,4-dioxanyl; 1,4,7-trithiacyclononanyl; tetrahydropyranyl; and/or oxazolidinyl, amines are —N(R)$_2$, wherein each R, independent of each other, is selected from the group comprising: H; $C_1$-$C_6$-alkyl; $C_1$-$C_6$-alkyl-$C_6H_5$; and/or phenyl, whereby both R can form a —NC3 to —NC5 heterocyclic ring closure, halogen is F; Cl; Br and/or I, especially preferably F, sulfonate is —S(O)$_2$OR, wherein R=H; $C_1$-$C_6$-alkyl; phenyl; $C_1$-$C_6$-alkyl-$C_6H_5$; Li; Na; K; Cs; Mg; and/or Ca, sulfate is —OS(O)$_2$OR, wherein R=H; $C_1$-$C_6$-alkyl; phenyl; $C_1$-$C_6$-alkyl-$C_6H_5$; Li; Na; K; Cs; Mg; and/or Ca, sulfone is —S(O)$_2$R, wherein R=H; $C_1$-$C_6$-alkyl; phenyl; $C_1$-$C_6$-alkyl-$C_6H_5$ and/or amines (for the formation of sulphonamide) is selected from the group comprising: —NR'$_2$, wherein each R', independently of each other, is selected from the group comprising: H; $C_1$-$C_6$-alkyl; $C_1$-$C_6$-alkyl-$C_6H_5$; and/or phenyl, wherein if both R' are $C_1$-$C_6$-alkyl, the R' together can form a —NC3 to —NC5 heterocyclic ring closure, carboxylate derivatives are —C(O)OR, wherein R is selected from the group comprising: H; $C_1$-$C_{20}$-alkyl; phenyl; $C_1$-$C_6$-alkyl-$C_6H_5$; Li; Na; K; Cs; Mg; and/or Ca, carbonyl derivatives are —C(O)R, wherein R is selected from the group comprising: H; $C_1$-$C_6$-alkyl; phenyl; $C_1$-$C_6$-alkyl-$C_6H_5$ and/or amine (for the formation of amide) is selected from the group comprising: —NR'$_2$, wherein R', independently of each other, is selected from the group comprising: H; $C_1$-$C_6$-alkyl; $C_1$-$C_6$-alkyl-$C_6H_5$; and/or phenyl, wherein if both R'=$C_1$-$C_6$-alkyl, the R' together can form a —NC3 to —NC5 heterocyclic ring closure, phosphonate is —P(O)(OR)$_2$, wherein each R, independently of each other, is selected from the group comprising: H; $C_1$-$C_6$-alkyl; phenyl; $C_1$-$C_6$-alkyl-$C_6H_5$; Li; Na; K; Cs; Mg; and/or Ca, phosphate is —OP(O)(OR)$_2$, wherein each R, independently of each other, is selected from the group comprising: H; $C_1$-$C_6$-alkyl; phenyl; $C_1$-$C_6$-alkyl-$C_6H_5$; Li; Na; K; Cs; Mg; and/or Ca, phosphine is —P(R)$_2$, wherein each R, independently of each other, is selected from the group comprising: H; $C_1$-$C_6$-alkyl; phenyl; $C_1$-$C_6$-alkyl-$C_6H_5$, phosphine oxide is —P(O)R$_2$, wherein each R, independently of each other, is selected from the group comprising: H; $C_1$-$C_6$-alkyl; phenyl; $C_1$-$C_6$-alkyl-$C_6H_5$ and/or amine (for the formation of phosphone amidate) is selected from the group comprising: —NR'$_2$, wherein R', independently of each other, is selected from the group comprising: H; $C_1$-$C_6$-alkyl; $C_1$-$C_6$-alkyl-$C_6H_5$; and/or phenyl, wherein, if both R'=$C_1$-$C_6$-alkyl, the R' together can form a —NC3 to —NC5 heterocyclic ring closure.

In particular, compounds selected from the group comprising the general formulas (1), (2), (3), (4), (5), (6), (7) and/or (8) preferably selected from the group comprising compounds (9), (10), (11), (12), (13) and/or (14), (20) and/or (21) and/or their enantiomers, diastereomers as well as their pharmaceutically well-tolerated salts are advantageous for the production of inhibitors suitable for blocking proteins having at least one sec7-domain.

The objective of the invention is also achieved by compounds that bind to proteins having at least one sec7-domain, whereby the compounds are selected from the group comprising the general formulas (1), (2), (3), (4), (5), (6), (7) and/or (8) preferably selected from the group comprising compounds (9), (10), (11), (12), (13) and/or (14), (20) and/or (21) and/or their enantiomers, diastereomers as well as their pharmaceutically well-tolerated salts.

The objective of the invention is also achieved by compounds that are selected from the group comprising the general formulas (20) and/or (21) and/or their enantiomers, diastereomers as well as their pharmaceutically well-tolerated salts. These compounds are suitable, for example, for the production of drugs for the treatment of diseases that can be influenced by the activity of the guanine nucleotide exchange factors, especially of the cytohesins, such as, for instance, autoimmune diseases such as rheumatoid arthrites, multiple sclerosis, diabetes mellitus (type 1), psoriasis, Crohn's disease, allergies, tumor diseases such as lung or bronchial cancer, prostate cancer, colon or rectal cancer, lymphatic cancer or leukemia, bladder cancer, breast and/or ovarian cancer and/or immunosuppression, for example, in cases of organ transplants.

Cytohesins are involved, for example, in the activation of integrins. Without being committed to a given theory, it is assumed that these compounds can be used in the realm of medicine for a large number of diseases, especially due to the inhibition of the cytohesins by compounds selected from the group comprising the general formulas (1), (2), (3), (4), (5), (6), (7) and/or (8) preferably selected from the group comprising compounds (9), (10), (11), (12), (13), (14) and/or (19), (20) and/or (21), for example, via an interaction of the cytohesins with integrins, via the inhibition of the adhesion of leucocytes to cell surfaces and/or via influencing inflammatory processes.

The compounds provided can be advantageously employed to offer a specific inhibitory effect on cytohesin-dependent immune reactions of the cells. Without being committed to a given theory, it is assumed that the provided compounds can have an inhibitory effect on the adhesion and migration of dendritic cells. The targeted migration of dendritic cells is a prerequisite for the formation of an adaptive immune response. In preferred embodiments, the compounds according to the invention can be used in order to effectuate a targeted influencing, especially an inhibition, of the adaptive cellular immune response in cells, tissues and/or organs.

The provided compounds can show, for instance in in vitro experiments, that the adhesion and/or migration of dendritic cells to ICAM-1 (intercellular adhesion molecule-1) can already be inhibited at low concentrations as needed in order to bring about an effect on the inhibition of insulin-dependent signal transduction cascades. This advantageously makes it possible to use the provided compounds in order to influence various metabolic processes; especially taking into account the applicable therapeutic windows, a systematic targeted treatment of various diseases can be made possible.

Advantageously, the provided compounds can exhibit no toxicity or only a slight or negligible toxicity, especially cytotoxicity. In particular, the provided compounds can have no concentration-dependent and/or time-dependent toxicity or only a small or negligible concentration-dependent and/or time-dependent toxicity. This makes it possible to use the provided compounds for the treatment of diseases in humans as well as for the production of drugs.

A major advantage of the invention lies in the fact that the compounds selected from the group comprising the general formulas (1), (2), (3) (4), (5), (6), (7) and/or (8) preferably selected from the group comprising compounds (9), (10), (11), (12) (13), (14) and/or (19), (20) and/or (21) are suitable for the production of drugs for the treatment of diseases that can be influenced by the activity of the guanine nucleotide exchange factors, especially the cytohesins.

These diseases include, for example, diseases in which inflammatory processes play a role, cancer or tumor diseases, allergic diseases, autoimmune diseases and/or diseases in which immunosuppression plays a role.

Especially advantageous compounds are those selected from the group comprising the general formulas (1), (2), (3) (4), (5), (6), (7) and/or (8) preferably selected from the group comprising compounds (9), (10), (11), (12) (13), (14) and/or (19), (20) and/or (21) and/or their enantiomers, diastereomers as well as their pharmaceutically well-tolerated salts, for the production of a drug for the treatment of autoimmune diseases such as rheumatoid arthrites, multiple sclerosis, diabetes mellitus (type 1), diabetes mellitus (type 2), psoriasis, Crohn's disease, allergies, tumor diseases such as lung or bronchial cancer, colon or rectal cancer, prostate cancer, lymphatic cancer or leukemia, bladder cancer, breast and/or ovarian cancer and/or immunosuppression, for example, in cases of organ transplants.

Moreover, the provided compounds and/or their enantiomers, diastereomers as well as their pharmaceutically well-tolerated salts can be used for the production of a drug for the treatment of diabetes mellitus (type 2).

Another subject matter of the invention relates to a method for the identification of compounds that bind to proteins preferably having at least one sec7-domain, whereby the method comprises the following steps:
a) production of an RNA preferably labeled with fluorescein, comprising the steps:
 aa) optional amplification of a DNA sequence
 bb) optional purification of the amplified DNA sequence
 cc) optional transcription of the DNA sequence into an RNA sequence
 dd) labeling of the RNA, preferably labeling with fluorescein
 ee) purification of the labeled RNA
b) determination of the polarization of the labeled RNA
c) addition of a protein preferably having at least one sec7-domain
d) determination of the polarization of the complex consisting of protein and labeled RNA
e) addition of the compound to be examined
f) determination of the polarization after the addition of the compound to be examined.

The method is preferably based on the method of fluorescence polarization, in which an RNA molecule is preferably labeled with a fluorescence label such as fluorescein.

In order to produce a sufficient amount of usable RNA, first of all, the DNA molecule corresponding to the RNA sequence can be amplified. The amplification of a DNA sequence is preferably carried out by means of a polymerase chain reaction (PCR). The DNA can be processed and/or purified in a subsequent step, preferably by means of phenol/chloroform extraction and/or ethanol precipitation. The DNA sequence can then be transcribed into an RNA sequence.

In preferred embodiments of the method, the labeling of the RNA is carried out with a fluorophore.

Preferably, the RNA is transcribed in vitro in the presence of the RNA polymerase from phage T7. In preferred embodiments, this transcription is carried out in the presence of guanosine-5'-monophosphothioate. The transcription leads to an introduction of a thiophosphate group at the 5'-end of the RNA molecule. This thiol group can then react with an activated fluorophore reagent, for example, fluorescein or a fluorescein derivative such as 5-iodoacetyl-fluorescein.

In preferred embodiments, fluorescein-labeled RNA molecules exhibit low polarization. The term "polarization" means especially a fluorescence polarization. The determination of the polarization of the labeled RNA can be performed in a fluorescence polarimeter.

In a subsequent step, a protein preferably having a sec7-domain is added. Preferred proteins are preferably selected from the group comprising cytohesins such as cytohesin-1, cytohesin-2, cytohesin-3 and/or cytohesin-4, preferably cytohesin-1. The protein can be a native cytohesin protein as well as a protein that has a sec7-domain and that was expressed in vitro and purified and/or a peptide.

When the protein binds to the labeled RNA, the polarization of the complex made up of protein and labeled RNA increases in comparison to the polarization of the free RNA. The polarization of the complex made up of protein and labeled RNA can be determined in another step of the process.

Subsequently, the compound to be examined is added. An advantage of the process is achieved in that compounds that interfere with the RNA/protein binding can expel the RNA from the protein and can thus once again generate a lower polarization signal.

The polarization after the addition of the compound to be examined can be measured. Advantageously, a compound that binds to the protein can be detected by a drop in the polarization signal, especially to the value of the polarization of the free RNA.

In preferred embodiments of the method, reaction conditions are selected that comprise RNA in the range from 1 nM to 10 µM, preferably in the range from 10 nM to 1 µM, protein in the range from 10 nM to 100 µM, preferably in the range from 100 nM to 10 µM, and/or that comprise the compound to be examined in the range from 1 µM to 10 mM, preferably in the range from 10 µM to 1 mM. Special preference is given to reaction conditions comprising 100 nM RNA, 1 µM protein and/or 100 µM of the compound to be examined.

In an advantageous embodiment, the method can be used as a screening assay with a high throughput rate. This allows the examination of a high number of compounds. In especially advantageous embodiments, the method has a z-factor of 0.81, which represents a quality factor for the executability of the screening method.

In preferred embodiments, the DNA and/or RNA sequence is selected from the group comprising M69-aptamers, K61-aptamers and/or natural DNA and/or RNA. An especially preferably usable M69-aptamer, which binds the sec7-domain of cytohesin-1 and cytohesin-2, is described, for example, in Mayer, G. et al., Proc Natl Acad Sci USA 98, 4961-5 (2001). An especially preferably usable K61-aptamer, which specifically binds the sec7-domain of cytohesin-2, is described in Theis, M. G. et al., Proc Natl Acad Sci USA, 101, 11221-26 (2004).

The term "aptamers" as set forth in the invention, refers to peptides and/or oligonucleotides that interact specifically with cellular proteins.

Examples and figures that serve to illustrate the present invention are given below.

Figure 2:
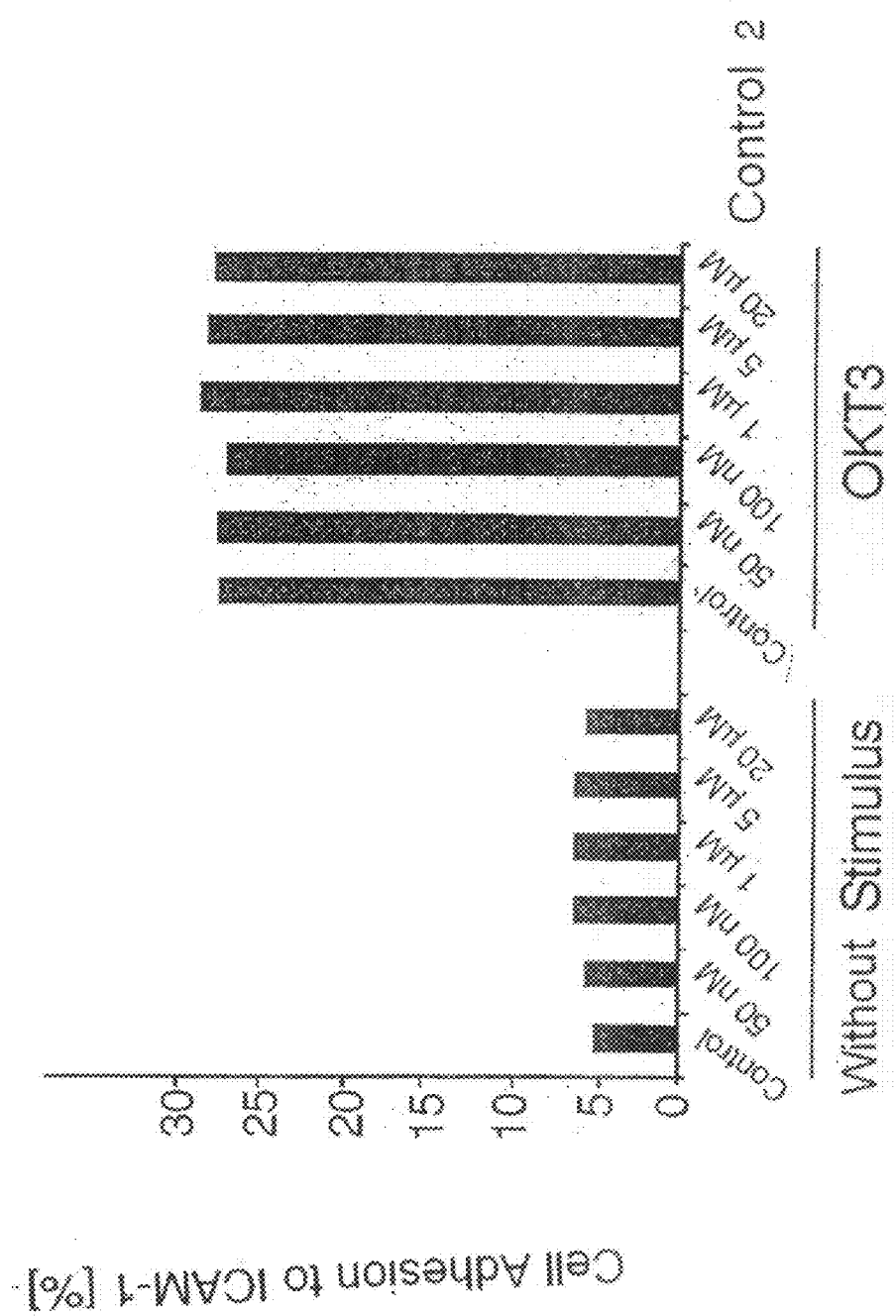
Figure 4:
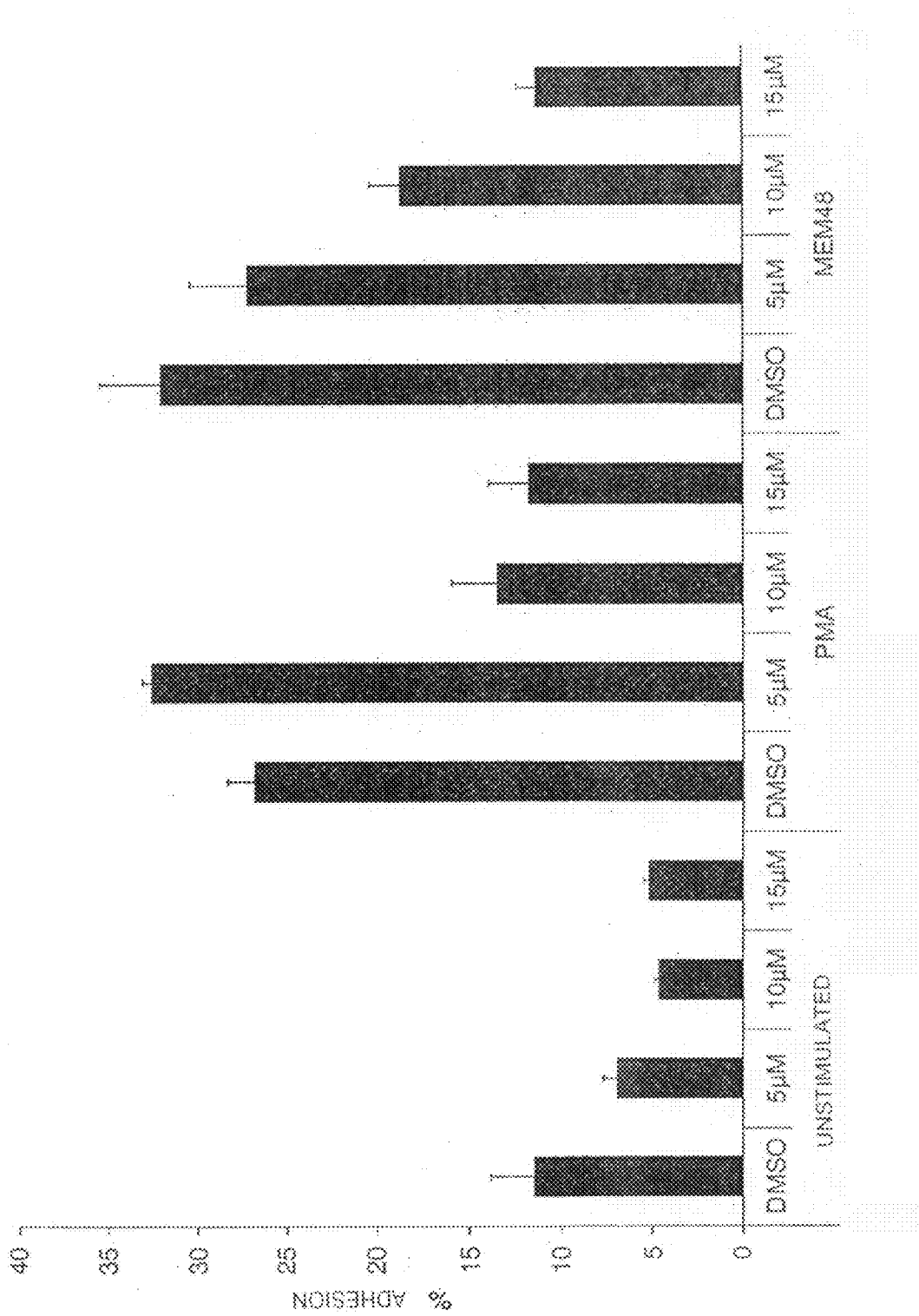
Figure 5:
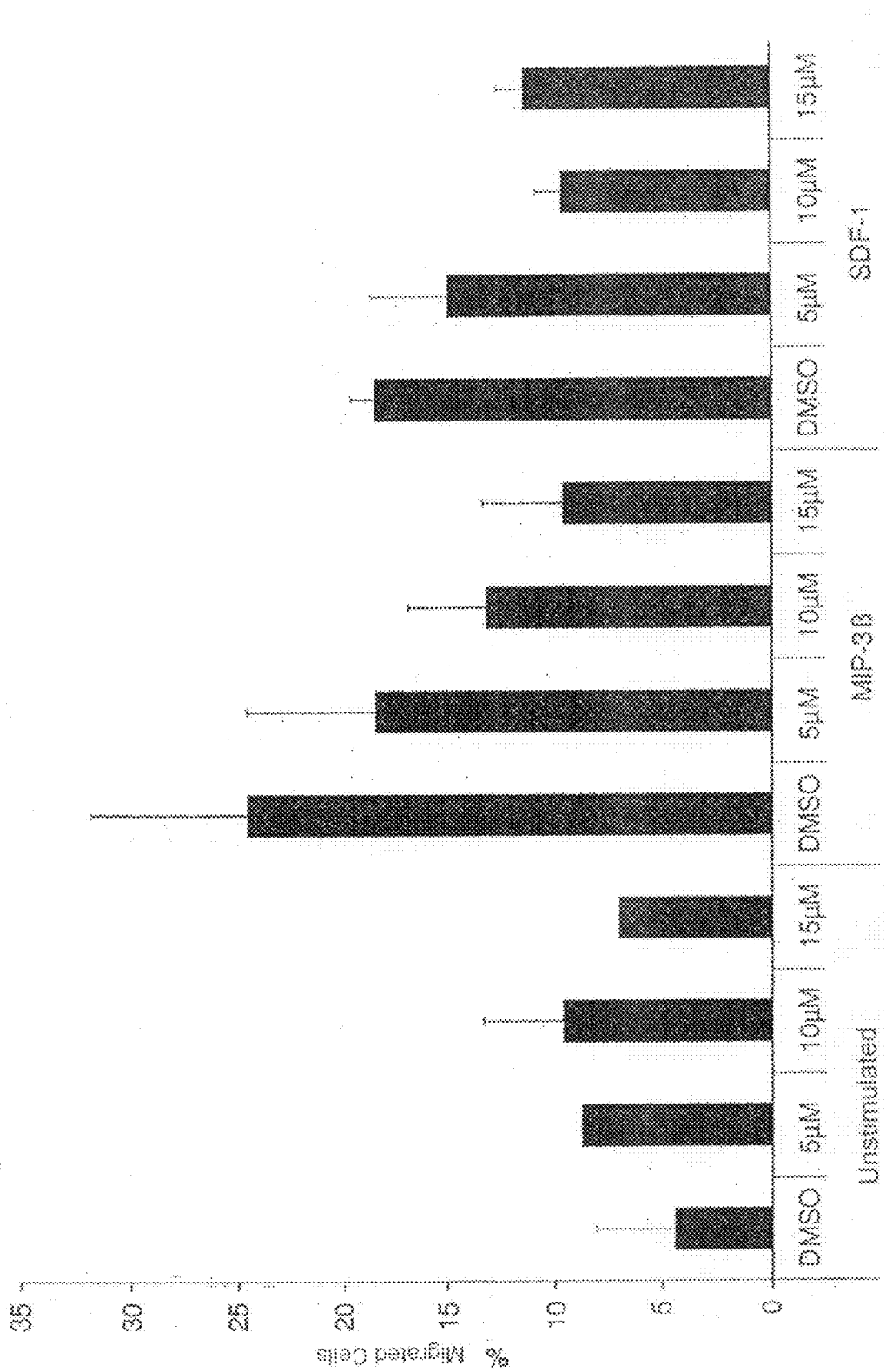

The figures show:

FIG. 1 the specific inhibitory effect of the compound (9) on cytohesin-dependent adhesion mechanisms in primary human lymphocytes after stimulation with the monoclonal antibody OKT3 and phorbolester (PMA);

FIG. 2 a control experiment with a compound that does not have an inhibitory effect (Control 2) in primary human lymphocytes after stimulation with the monoclonal antibody OKT3;

FIG. 3 the DNA sequence of the M69-aptamer, which can be used as a template, as well as the sequence of the primer that can be used for the amplification;

FIG. 4 the inhibitory effect of the compound according to Formula (9) on the adhesion of dendritic cells to the substrate ICAM-1;

FIG. 5 the inhibitory effect of the compound according to Formula (9) on the migration of dendritic cells to the substrate ICAM-1.

EXAMPLE 1

The $IC_{50}$ value for the inhibition of the exchange activity of the sec7-domains of various guanine nucleotide exchange factors of the compounds (9), (10), (11), (12), (14) and (19) was determined.

For this purpose, the sec7-domains of cytohesin-1, cytohesin-2 and Gea2 as well as the NΔ 17-ARF 1, a mutant of the ARF protein, recombinantly expressed in *E. coli* BL21DE3, were purified by means of a standard method and used as catalysts for the exchange from GDP to GTP in GTPases of the family of the ADP ribosylation factors. The exchange from GDP to GTP induces a conformation change of the ribosylation factor, as a result of which the fluorescence of a tryptophan radical of the protein is increased.

In 50 mM of HEPES, pH 7.4, 120 mM of KCl, 1 mM of $MgCl_2$, 45 μM of GTP S, the compounds (9), (10), (11), (12), (14) and (19), each in concentrations of 1 μM to 30 μM, were added to 1 μM NΔ 17-ARF1 and, in each case, 1 μM of the purified sec7-domain of cytohesin-1, cytohesin-2 and Gea2, and the fluorescence was measured in a Varioskan, Thermo LifeSciences Inc., at the following wavelengths: excitation: 275 nm, emission 340 nm.

The $IC_{50}$ value can be determined by plotting the initial rise of the fluorescence signal against the added concentrations of the compounds. The $IC_{50}$ value corresponds to the concentration of the compounds at which the activity of the protein is reduced to half. The lower the $IC_{50}$ value, the more strongly the compound inhibits the sec7-domain. Brefeldin A, a specific inhibitor of the high-molecular ADP ribosylation factor Gea2 served as the control.

TABLE 1

| Compound | $IC_{50}$ [μM] Cytohesin-1-sec7 | $IC_{50}$ [μM] Cytohesin-2-sec7 | $IC_{50}$ [μM] Gea2-sec7 |
| --- | --- | --- | --- |
| 9 | 7.6 ± 0.3 | 8.3 ± 0.2 | 64 ± 4 |
| 10 | 12.6 ± 0.3 | 16.1 ± 0.9 | 67 ± 5 |
| 11 | 8.8 ± 0.3 | 12.4 ± 0.3 | 42 ± 4 |
| 12 | 8.0 ± 0.3 | 19.5 ± 0.3 | 22 ± 2 |
| 14 | 14.8 ± 0.3 | 19.3 ± 0.3 | — |
| 19 | 15.0 ± 0.3 | 20.0 ± 0.6 | — |
| Brefeldin A | >150 | >150 | 23 ± 1 |

As can be seen in Table 1, the compounds (9), (10), (11), (12), (14) and (19), especially (9), (10), (11) and (12), exhibit a specific inhibition of the sec7-domains of the cytohesins vis-à-vis the sec7-domain of Gea2, whereas the reference compound Brefeldin A exhibits a specific inhibition of the sec7-domain of Gea2.

EXAMPLE 2

The $IC_{50}$ value was determined in comparison to the $LC_{50}$ value in a luciferase assay in HeLa-cells, corresponding to the test conditions described in Theis, M. G. et al., Proc Natl Acad Sci USA, 101, 11221-26 (2004). The stimulation of receptor tyrosine kinases by means of growth factors contained in fetal calf serum activates the MAPK path via cytohesin-2 and results in an activation of the serum response element. This activation manifests itself in the quantity of luciferase produced in the cells.

Compounds (9), (10), (11), (12), (14) and (19) were each added in concentrations of 1 μM to 50 μM to $6.5 \times 10^4$ HeLa-cells.

Table 2 shows a comparison of the $IC_{50}$ values to the $LC_{50}$ values after 24 hours. The $LC_{50}$ values were determined by an MTT assay according to a standard method.

The $LC_{50}$ value describes the lethal concentration at which 50 of the cells died within 24 hours after a one-time administration.

The $IC_{50}$ value was determined from the plotting of the concentration of the compound against the intensity of the luciferase signal.

TABLE 2

| Compound | $IC_{50}$ [μM] | $LC_{50}$ [μM] |
| --- | --- | --- |
| 9 | 12 ± 0.8 | 141 ± 8 |
| 10 | 23 ± 5 | >>150 |
| 11 | 5 ± 1.5 | 142 ± 12 |
| 12 | 5 ± 1.5 | >>150 |
| 14 | 3 ± 1 | — |
| 19 | 3.5 ± 0.5 | >150 |
| Control 1 | >50 | >>150 |

The following compound served as the negative control (control 1):

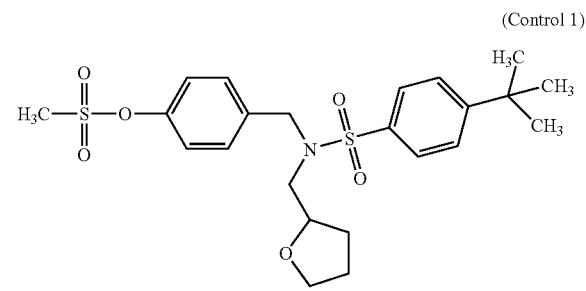

(Control 1)

As can be seen in Table 2, the compounds (9), (10), (11), (12), (14) and (19), especially (9), (10), (11) and (12), exhibited a very good inhibition of cytohesin-2 at low concentrations, while a toxicity only occurred at very high concentrations after 24 hours.

EXAMPLE 3

Human peripheral blood cells (PBL) were stimulated with agonists that activate a beta-2 integrin-dependent adhesion. In these primary human lymphocytes, the beta-2 integrin-dependent adhesion can be activated by cytohesins at the specific ligands ICAM-1.

The agonists employed were the monoclonal antibody OKT3 (hybridome of ATCC, mAb OKT3 purified on protein A, according to standard methods from Current Protocols in Immunology, 5th Ed., Coligan et al., Edts, Wiley 2004) against the CD3 complex, a T-cell receptor and phorbolester (PMA), which non-physiologically activates intracellular signal cascades in human PBL including integrin-dependent adhesion while circumventing cytohesins.

Cells from human blood were isolated according to standard methods (Current Protocols in Immunology, 5th Ed., 2004, Coligan et al., Edts, Wiley). Cell culture dishes coated with ICAM-1 were produced by means of recombinant ICAM-1-Fc fusion protein (Kolanus, W. et al., Cell 86, 233-42 (1996), Geiger, C. et al., EMBO J., 19, 2525-2536 (2000)). 300,000 human peripheral blood cells (PBL) were stimulated for 30 minutes with 2 µg/ml of OKT3 or 40 ng/ml of phorbolester (PMA) in Hank's BSS, (Gibco; composition (g/l): $CaCl_2 \cdot 2H_2O$ (0.185), KCl (0.4), $KH_2PO_4$ (0.06), $MgCl_2 \cdot 6H_2O$ (0.1), $MgSO_4 \cdot 7H_2O$ (0.1), NaCl (8.0), $NaHCO_3$ (0.35), $Na_2HPO_4$ (0.048), D-glucose (1.0)), and placed for one hour in Hank's BSS onto the ICAM-1 coated cell culture dishes, whereby the agonists were not removed. Non-bound cells were removed by washing with Hank's BSS. The percentage of bound cells was determined by counting under a microscope using a standard counting grid.

As can be seen in FIG. 1, the compound (9) inhibited the adhesion of the human peripheral blood cells (PBL) to ICAM-1 in a concentration-dependent manner. The $IC_{50}$ value was approximately 500 nM to 1 µM. As can also be seen in FIG. 1, the inhibitory effect only occurred in cells stimulated with OKT3, whereas cells activated by phorbolester (PMA) were not influenced by the compound (9). This shows the high specificity of the compound (9) with respect to cytohesin-dependent adhesion mechanisms.

The specificity of the inhibition of the OKT3-mediated adhesion in primary human lymphocytes by compound (9) is likewise shown in FIG. 2. FIG. 2 shows that a control compound (Control 2) had no effect on this system.

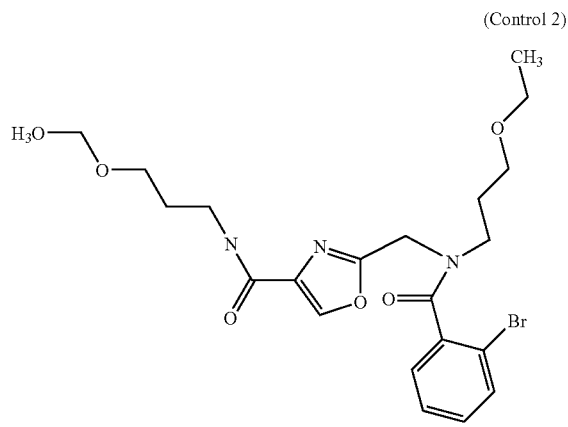

(Control 2)

EXAMPLE

Fluorescence Polarization Assay

The DNA sequence of the M69-aptamer (SEQ ID NO: 1) shown in FIG. 3 was amplified using the likewise shown primer (SEQ ID NO: 2, SEQ ID NO: 3) by means of PCR. In this process, 0.01 µM of DNA templates, in each case 1 µM 3'- and 5'-Primer, 1.5 mM of MgCl2, 0.2 mM of dNTP-mix, and Taq polymerase were used.

The PCR program employed comprised the following steps:

denaturing 95° C. [203° F.] 1 min 15 cycles
annealing 55° C. [131° F.] 1 min
extension 72° C. [161.6° F.] 1 min.

The DNA was subjected to a phenol/chloroform extraction according to standard methods and was precipitated in ethanol before it was transcribed for 4 hours at 37° C. in the presence of 20 mM of guanosine-5'-monophosphothioate, T7-RNA polymerase. The RNA was then precipitated by means of ethanol, dissolved in DEPC water and purified over a G25 column (Amersham Biosciences).

10 µM RNA was heated with 1× labeling buffer (50 mM tris, pH 8.0, 5 mM EDTA), 2 M Urea and water for 3 minutes to 95° C. [203° F.] and then allowed to cool off for 10 minutes. 2.5 mg of activated 5-iodoacetyl fluorescein were dissolved in 500 µM of DMF and added to the batches. The mixture had a concentration of 2 mM of 5-iodoacetyl fluorescein. This mixture was incubated for 2 hours at 37° C. [98.6° F.] under slight agitation under aluminum foil. Then 3 volumes of 100% ethanol were added, ⅒ volume of 3M NaOAc, pH 5.4, and 1 µl of glycogen were added and this was incubated for 20 minutes at −80° C. [−112° F.], before centrifugation was carried out at 14,000 rpm for 20 minutes at 4° C. [39.2° F.]. The pellet was washed with 100 µl of 70% ethanol and dissolved in 20 µl of DEPC water.

Subsequently, the RNA was fractionated in an 8% polyacrylamide gel, the RNA was eluted out of the gel in 500 µl of 0.3 M NaOAc solution for 1.5 hours at 65° C. [149° F.], filtered through a syringe filled with glass wool, precipitated with ethanol and dissolved in DEPC water The reaction volume of the fluorescence polarization measurements was 50 µl PBS, pH 7.4, 3 mM $MgCl_2$. The measurements were made in 384-well plates (Greiner BioOne) in an Ultra Type polarimeter, TECAN; excitation: 485 nm, emission: 535 nm. The z-factor was 0.81. The fluorescence polarization of the fluorescein-labeled RNA, the fluorescence polarization after the addition of purified sec7-domain of cytohesin-1, cytohesin-1-sec7, (see Example 1), and the fluorescence polarization after the addition of each compound to be examined were all determined.

The concentrations of the individual measurements were:

| | |
|---|---|
| M69 | 100 nM |
| cytohesin-1-sec7 | 1 µM |
| compound | 100 µM. |

All of the measurements were carried out in duplicate.

EXAMPLE 5

Determination of the Effect of the Compound According to Formula (9) on the Adhesion and Migration Capability of Human Dendritic Cells In Vitro 1. Generation of Human Dendritic Cells from Monocytes
Dendritic cells were produced in vitro by means of differentiation factors (IL-4 and GM-CSF) from blood monocytes that were isolated from peripheral mononuclear cells (PBMC) by Ficoll density gradient centrifugation from the human blood of anonymous donors.

The blood was mixed at a ratio of 1:1 with PBS (KCl 0.2 g/l, $KH_2PO_4$ 0.2 g/l, NaCl 8 g/l, $Na_2HPO_4$ 1.15 g/l, PAA, Cölbe)/2 mM EDTA and layered onto half the volume of Ficoll. Centrifugation was carried out at 300×g, 30 minutes with no brake. After the centrifugation, a centered white band appeared which contained the PBMC. This was picked up with PBS/2 mM EDTA, filled up to 50 ml and subjected to several washing steps at 640×g, 500×g, 400×g, 300×g and 200×g. Subsequently, the cells were picked up in a titer of $5\times10^6$/ml in "VLE-RPMI+/+"-medium (Biochrom, Berlin, containing 10% fetal calf serum (FCS) and 1% penicillin/streptomycin) and incubated for 90 minutes in an incubator at 37° C. [98.6° F.] and 5% $CO_2$. During this time, the monocytes adhere to the bottom of the culture dish. Peripheral blood lymphocytes remained in suspension, and were picked up. Adhering monocytes were washed three or four times with PBS and picked up in "VLE-RPMI+/+"-medium, every time containing 20 ng/ml of the human recombinant cytokines IL-4 and GM-CSF (Granulocyte Macrophage-Colony Stimulating Factor, R&D Systems, Wiesbaden). These cytokines induce the differentiation between the monocytes and immature dendritic cells within 5 to 7 days. The cells were cultivated for 5 to 7 days, and every other day, half of the medium was replaced by fresh medium plus the cytokines. By adding 1 µg/ml of lipopolysaccharide (LPS, Sigma, Taufkirchen) and 50 ng/ml of the cytokine TNF-a (Strathmann, Hamburg), on days 5 to 7 of the cultivation, a differentiation between the immature and the mature dendritic cells was induced within two days, whereby the cells were used for experiments on the second day after the addition.

2. Determination of the Cellular Chemotaxis (Targeted Migration) In Vitro

The quantitative analysis of the cell migration was carried out in modified Boyden chambers consisting of a 24-hole plate into which the Transwell® filters with a 5 µm pore size had been placed. Consequently, the modified Boyden chambers contained a chamber above the filter and a chamber below the filter. The filters were coated with supernatants of fibroblasts that secrete ICAM-1. Mature dendritic cells were incubated for 96 hours with 1 µM, 10 µM or 15 µM of the compound according to Formula (9) in "VLE-RPMI+/+"-medium. All of the batches contained 0.5% DMSO. The controls contained exclusively 0.5% DMSO without the compound according to Formula (9). In order to perform the cell migration test, for each batch, $1.5\times10^5$ cells were dissolved in 300 µl of "starvation medium" ("−/− VLE-RPMI", containing 0.5% FCS) and placed into the upper chamber of a modified Boyden chamber. 700 µl of the "starvation medium" were placed into the lower chamber. The cells were incubated for 45 minutes in the incubator at 37° C. [98.6° F.] and 5% $CO_2$. During this time, the cells settled on the filter. Subsequently, the medium of the lower chamber was replaced with medium with the corresponding chemokine CCL19/MIP-3β (Strathmann, Hamburg 100 ng/ml) or CXCL12/SDF-1 (Strathmann, Hamburg, 200 ng/ml)). For each batch, a control was used in which the lower chamber contained "starvation medium" without chemokines. The cells were incubated for 4 hours at 37° C. [98.6° F.] and 5% $CO_2$ in the incubator and subsequently, the number of cells that had migrated into the lower chamber in the direction of the chemokine was determined. In each case, duplicate batches were used.

Under corresponding conditions, the adhesion was determined after stimulation with phorbolester (PMA, 50 ng/ml, Sigma, Taufkirchen) or anti-beta-2 integrin antibodies MEM-48 (5 µg/ml, Vaclav Horeijsi, Czech Academy of Sciences Prague).

As the control, in each case, the migration of cells that had not been treated with the compound according to Formula (9) after stimulation with the chemokines CCL19 or CXCL12 or the adhesion of cells not treated with the compound according to Formula (9) after stimulation with phorbolester PMA or with the anti-beta-2 integrin antibody MEM-48, in 0.5% DMSO was plotted.

As can be seen in FIGS. 4 and 5, the compound according to Formula (9) brought about a concentration-dependent inhibition of the adhesion and migration of dendritic cells on the substrate ICAM-1. The adhesion capacity is a fundamental pre-requisite for the migration of the white blood cells. Therefore, it is assumed that the ability on the part of the dendritic cells to migrate was disrupted due to the inhibition von cytohesin-1 by the compound according to Formula (9).

EXAMPLE 6

Determination of the Toxicity of the Compound According to Formula (9)

The cytotoxicity of the compound according to Formula (9) was determined by means of propidium iodide (PI) employing flow cytometry. PI is a DNA stain that cannot penetrate into living cells. The experiments were carried out in an incubator at 37° C. [98.6° F.] and 5% $CO_2$.

Peripheral blood lymphocytes were incubated with concentrations of 50 nM, 100 nM, 1 µM, 5 µM, 20 µM or 50 µM of the compound according to Formula (9) in "VLE-RPMI+/+" (Biochrom). The DMSO concentration per batch was 0.5%. A control batch contained 0.5% DMSO. After 2 hours, 24 hours and 72 hours, cells were removed and incubated with 2 µg/ml of PI for 5 minutes. The cells were centrifuged at 200×g for 8 minutes, washed with PBS, centrifuged again and analyzed in a flow cytometer (Beckmann Coulter, Krefeld).

It could be ascertained that the percentage of PI-positive, that is to say, dead, cells did not rise in a concentration-dependent or time-dependent manner. The percentage of dead cells, especially after 24 and 72 hours of incubation, exhibited only slight deviations from the controls. Thus, it is assumed that the compound according to Formula (9) has no cytotoxicity or at least no clearly detectable cytotoxicity.

The invention claimed is:

1. A pharmaceutical composition comprising a compound of formula (9) as indicated below and/or its enantiomers, diastereomers as well as its pharmaceutically well-tolerated salts:

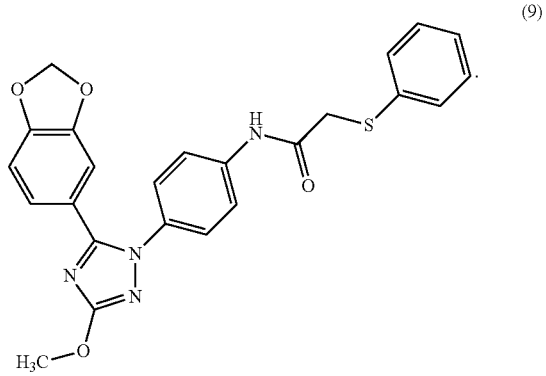

(9)

2. The pharmaceutical composition according to claim 1, characterized in that the pharmaceutical composition, referring to a daily dosage, comprises 10 nM to 100 μM of the compound of formula (9) and/or its enantiomers, diastereomers as well as its pharmaceutically well-tolerated salts.

3. The pharmaceutical composition according to claim 1, characterized in that the compounds are inhibitors of proteins selected from the group of guanine nucleotide exchange factors.

4. The pharmaceutical composition according to claim 3, characterized in that the guanine nucleotide exchange factors are guanine nucleotide exchange factors for human ADP ribosylation factors selected from the group of Gea1, Gea2, B1G1, B1G2 and/or cytohesins such as cytohesin-1, cytohesin-2, cytohesin-3 and/or cytohesin-4.

5. The pharmaceutical composition according to claim 1, characterized in that the pharmaceutical composition, referring to a daily dosage, comprises 100 nM to 10 μM of the compound formula (9) and/or its enantiomers, diastereomers as well as its pharmaceutically well-tolerated salts.

6. The pharmaceutical composition according to claim 1, characterized in that the pharmaceutical composition, referring to a daily dosage, comprises 1 μM to 10 μM of the compound formula (9) and/or its enantiomers, diastereomers as well as its pharmaceutically well-tolerated salts.

7. The pharmaceutical composition according to claim 1, characterized in that the pharmaceutical composition, referring to a daily dosage, comprises 1 μM to 3 μM of the compound formula (9) and/or its enantiomers, diastereomers as well as its pharmaceutically well-tolerated salts.

8. A pharmaceutical composition comprising a compound of formula (9) and/or its enantiomers, diastereomers as well as its pharmaceutically well-tolerated salts, for the production of a drug for the treatment of autoimmune diseases selected from the group consisting of rheumatoid arthritis, multiple sclerosis, diabetes mellitus (type 1), diabetes mellitus (type 2), psoriasis, Crohn's disease, allergies, tumor diseases selected from the group consisting of lung or bronchial cancer, colon or rectal cancer, prostate cancer, lymphatic cancer or leukemia, bladder cancer, breast and/or ovarian cancer and/or immunosuppression.

9. The pharmaceutical composition according to claim 8, comprising the compound of formula (9) and/or its enantiomers, diastereomers as well as its pharmaceutically well-tolerated salts, for the production of a drug for immunosuppression in cases of organ transplants.

* * * * *

SEQUENCE LISTING

<160> NUMBER OF SEQ ID NOS: 3

<210> SEQ ID NO 1
<211> LENGTH: 94
<212> TYPE: DNA
<213> ORGANISM: Artificial
<220> FEATURE:
<223> OTHER INFORMATION: M69-Aptamer

```
<400> SEQUENCE: 1
gggagagaca agcttgggtc tattatgcct ttagctagcg cattctgtgg ggtgggtgga      60
agaagagaaa gagaagttaa ttaaggatcc tcag                                 94

<210> SEQ ID NO 2
<211> LENGTH: 39
<212> TYPE: DNA
<213> ORGANISM: Artificial
<220> FEATURE:
<223> OTHER INFORMATION: 5'-Primer

<400> SEQUENCE: 2
tctaatacga ctcactatag ggagagacaa gcttgggtc                            39

<210> SEQ ID NO 3
<211> LENGTH: 20
<212> TYPE: DNA
<213> ORGANISM: Artificial
<220> FEATURE:
<223> OTHER INFORMATION: 3'-Primer

<400> SEQUENCE: 3
ctgaggatcc ttaattaact                                                 20
```